United States Patent [19]
Detjen et al.

[11] Patent Number: 5,970,466
[45] Date of Patent: Oct. 19, 1999

[54] GRAPHICAL COMPUTER SYSTEM AND METHOD FOR APPOINTMENT SCHEDULING

[75] Inventors: Ronald A. Detjen, Berlin; William R. Randolph, Menasha, both of Wis.

[73] Assignee: ImproMed, Inc., Oshkosh, Wis.

[21] Appl. No.: 08/944,185

[22] Filed: Oct. 6, 1997

[51] Int. Cl.$^6$ .................................................. G06F 17/60
[52] U.S. Cl. .................... 705/8; 705/1; 705/2; 705/3; 705/9
[58] Field of Search ................... 705/2, 3, 8, 9; 345/963; 364/468.05, 468.06, 705.06, 705.07

[56] References Cited

U.S. PATENT DOCUMENTS

| | | | |
|---|---|---|---|
| 5,323,314 | 6/1994 | Baber et al. ................................ | 705/8 |
| 5,634,100 | 5/1997 | Capps ......................................... | 705/9 |
| 5,761,646 | 6/1998 | Frid-Nielsen et al. ...................... | 705/9 |
| 5,832,448 | 11/1998 | Brown ........................................ | 705/2 |
| 5,842,173 | 11/1998 | Strum et al. ................................ | 705/1 |
| 5,842,175 | 11/1998 | Andros et al. .............................. | 705/3 |

OTHER PUBLICATIONS

Microsoft Works, Version 4 for the Macintosh, Chapter 9, "Guide to the Calendar", pp. 489–524.
Computer Dictionary, 4th Ed., Sams & Co. Inc., 1985, Charles J. Sippl, pp. 212 and 434, 1985.

*Primary Examiner*—Stephen R. Tkacs
*Assistant Examiner*—George D. Morgan
*Attorney, Agent, or Firm*—Quarles & Brady LLP

[57] ABSTRACT

A computer program stored in a storage medium and a computer-implemented method for scheduling appointments for an office or business includes program code for displaying screen displays on a computer monitor, including a day view screen display (18) with a plurality of thermometer-style schedules (43) having a vertical bar graph (44) opposite a daily appointment file (45) having multiple rows for entering appointment data. A horizontal scroll bar (48) allows the schedules to be displayed over a distance that is wider than a display area on the screen. The vertical bar graph (44) includes color-coded bars (47) to signify the status of appointments as: i) prior to check-in, ii) after check-in and iii) canceled appointments. In a "day view" schedules are arranged by selecting a group from a group list (24). The appointments can be predetermined as to type and duration, and a scheduler can refer to a list (63) of such pre-configured appointments (65) in scheduling patients. Various types of color-coding arrangements and icons are provided for patient status.

28 Claims, 11 Drawing Sheets

| Group | Resource | Start Time > | End Time | Comments |
|---|---|---|---|---|
| Doctors | Julie Johnson | 08:15 AM | 08:30 AM | Wheeler, Alice, 1628, 221 Bridgepast, CO, 26626, 22 |
| Doctors | Julie Johnson | 08:15 AM | 08:55 AM | Wheeler, Alice, 1628, 221 Bridgepast, CO, 26626, 22 |
| Doctors | Julie Johnson | 09:00 AM | 09:30 AM | Wheeler, Alice, 1628, 221 Bridgepast, CO, 26626, 22 |
| Doctors | Marlin | 09:10 AM | 09:50 AM | Wheeler, Alice, 1628, 221 Bridgepast, CO, 26626, 22 |
| | | 09:10 AM | 09:40 AM | Wheeler, Alice, 1628, 221 Bridgepast, CO, 26626, 22 |
| | | 02:15 PM | 12:35 PM | Wheeler, Alice, 1628, 221 Bridgepast, CO, 26626, 22 |
| | | 01:00 PM | 01:15 PM | Wheeler, Alice, 1628, 221 Bridgepast, CO, 26626, 22 |

Popup menu:
- Modify Appointment...
- Delete Appointment
- Add Customer Info
- Cut
- Copy
- ✓ Not Checked-In
- Checked-In
- Canceled Easy Time - C:\Program Files\EasyTime\Appt97.imp File  Edit  View  Reports  Setup  Help Doctors ▽  Julie Johnson ▽  09/03/1997 - Wednesday ▽

Day  Week  Month  Year

List By:
⊙ List All  ○ Group  ○ Resource

September 1997

| Sun | Mon | Tue | Wed | Thu | Fri | Sat |
|---|---|---|---|---|---|---|
| | 1 | 2 | 3 | 4 | 5 | 6 |
| | 4 | 4 | 7 | 4 | 4 | 6 |
| 7 | 8 | 9 | 10 | 11 | 12 | 13 |
| 5 | 4 | 6 | 4 | 5 | 4 | 6 |
| 14 | 15 | 16 | 17 | 18 | 19 | 20 |
| 4 | 7 | 4 | 4 | 6 | 4 | 5 |
| 21 | 22 | 23 | 24 | 25 | 26 | 27 |
| 6 | 6 | 5 | 6 | 4 | 4 | 7 |
| 28 | 29 | 30 | | | | |
| 4 | 4 | 6 | | | | |

| | Stat | Pat Ext | Name | Species | Sex | Date of Birth | Age | Weigh |
|---|---|---|---|---|---|---|---|---|
| ✓ | | C | Scottie | F | MN | 08 /01 /1981 | 16.1 | 9 |
| | | E | Mike | F | MN | 01 /01 /1982 | 15.7 | 1 |
| | | H | Rags | C | MN | 01 /01 /1990 | 7.7 | 2 |
| | | J | Merry | F | F | | | 7 |

Patient List

Client: Wheeler, Alice   Acct: 1628

Vaccination Summary

STOP Rabies 04 /01 /1997
GO Feline Booster 12 /17 /1997
GO Leukemia 12 /17 /1997
? FIP Vaccine STOP Fecal Exam 04 /13 /1993
? Heartworm Test
? Geriatric Exam
STOP Dental Cleaning 03 /23 /1995
✚ HYPER THYROID OK   Cancel

FIG. 10

Add Appointment Type

- Name: Annual Vaccinations–Canine
- Description: 
- Duration: 0 (hours) 10 (minutes)
- Group: Doctors

[OK] [Cancel] [Apply]

FIG. 11

Find Appointment

Search Criteria
- Enter Search String: Whe
- Optional Search Criteria
- Group: 
- Resource: 
- Start Date After/From: __/__/__  Before/To: __/__/__
- Start Time After/From: Before/To:
- Appointment Status: ☐ Not Checked-In  ☐ Checked-In  ☐ Canceled

| Date | Start Time | Resource | Comments |
|---|---|---|---|
| | | ia Fuentes | Wheeler, Alice, 1628, 225 Overland Avenue, Bridgeport, CT,, 06606, |

Modify Appointment...
Delete Appointment
Cut
Copy
✓ Not Checked-in
Checked-in
Canceled

[Search] [Cancel] [Clear]

5,970,466

GRAPHICAL COMPUTER SYSTEM AND METHOD FOR APPOINTMENT SCHEDULING

TECHNICAL FIELD

The invention relates to computer-implemented methods and systems for scheduling appointments with clients and customers at medical offices, auto repair facilities, beauty salons and other types of businesses.

DESCRIPTION OF THE BACKGROUND ART

Computer programs for appointment scheduling have been known in the art. Such programs have been provided for use by users to make their own respective schedules. There has not been a program in which one or more staff members can schedule appointments for a group of professionals or for a group of facility or equipment resources.

In the field of veterinary medicine, as in other medical fields, there is a need to schedule appointments for veterinary doctors and other veterinary professionals and resources in a group practice over days, weeks and months of the year.

According to usual procedures, appointments are scheduled by office personnel in response to contacts with the owner of patient animals for a large number of professionals and resources in a group practice. Any computer program for this purpose should be easy to use. The screen displays should avoid visual clutter and should provide visual keys which assist the user in detecting matters that need attention. The program should include aids to the scheduler for scheduling various kinds of medical appointments.

Such a program should take advantage of the most up-to-date operating systems available for personal computers, including capabilities for networking of computers in an office environment.

SUMMARY OF THE INVENTION

The invention provides a computer-implemented method and computer program for displaying a plurality of schedules for a corresponding group of persons or resources, each schedule including i) a title bar identifying the individual or resource, ii) a vertical time graph extending over at least one day having colored bars corresponding in color and length to corresponding types and lengths of appointments, respectively, and iii) a plurality of appointment rows corresponding to time slots available for appointments during the day.

The invention also allows entry of standardized appointment types by name, group and duration. When scheduling appointments, a scheduler can select from a list of appointment types and use the pre-defined duration to set an end time in relation to a desired start time for the appointment.

In a further aspect of the invention, the plurality of schedules in the selected group are displayed horizontally on a page having a width that is greater than the width of a display area of the computer screen, and a horizontal scroll bar for the group of appointment schedules is provided to allow scrolling across the plurality of schedules.

The invention also allows for weekly views of a plurality of schedules for a selected person or resource, and a monthly view of all appointments for the month, or for a specific date in the month for a specific group or resource.

The invention further provides for sorting of the appointment file, and for convenient modification of appointments using a pop-up menu.

The invention further provides for displaying a patient dialog box including identification of multiple patients, and a color designating overall status of the patient, a health warning icon for any health warning conditions and a plurality of status icons representing status of certain medical conditions associated with an individual patient.

The invention further provides a "month view" screen display including a monthly calendar showing the number of appointments for each day, a file of appointments organized in columns by field, and radio buttons responsive to user inputs for listing all appointments for the month or for listing appointments by at least one of: by day, by group and by resource. In response to a right hand button mouse click, a pop-up menu is displayed for modifying appointments in the appointment list.

The invention further provides a "find appointments" command, which when executed, displays a "find appointments" dialog box for receiving data defining a specific resource, a date range, a time range and an appointment status to define the scope of the retrieval of appointments in the database file for display.

The invention further provides for a report of "missing appointments" command, and displays a dialog box for receiving data defining a specific group and a date range to limit the appointments listed in a missed appointments report.

The invention further provides an "options" command for displaying a dialog box for receiving data defining criteria for importing patient data from a patient database file.

The invention further provides a "preferences" command for displaying a dialog box for receiving data defining a rate at which new data input into the computer system is used to update the appointments file.

Other objects and advantages of the invention, besides those discussed above, will be apparent to those of ordinary skill in the art from the description of the preferred embodiment which follows. In the description, reference is made to the accompanying drawings, which form a part hereof, and which illustrate examples of the invention. Such examples, however, are not exhaustive of the various embodiments of the invention, and therefore, reference is made to the claims which follow the description for determining the scope of the invention.

BRIEF DESCRIPTION OF THE DRAWINGS

FIG. 2 is an elevational view of a "day view" screen display for the application program running on the computer of FIG. 1;

FIG. 4 is a second elevational view of the "month view" screen display seen in FIG. 3;

FIG. 5 is an elevational view of an "Add Appointment" dialog box for the application program running on the computer of FIG. 1;

FIG. 6 is an elevational view of a "Patient List" status box for the application program running on the computer of FIG. 1;

FIG. 10 is an elevational view of an "Add Appointment Type" dialog box for the application program running on the computer of FIG. 1;

FIG. 11 is an elevational view of a "Find Appointment" dialog box for the application program running on the computer of FIG. 1;

DETAILED DESCRIPTION OF THE PREFERRED EMBODIMENTS

Figure 1:
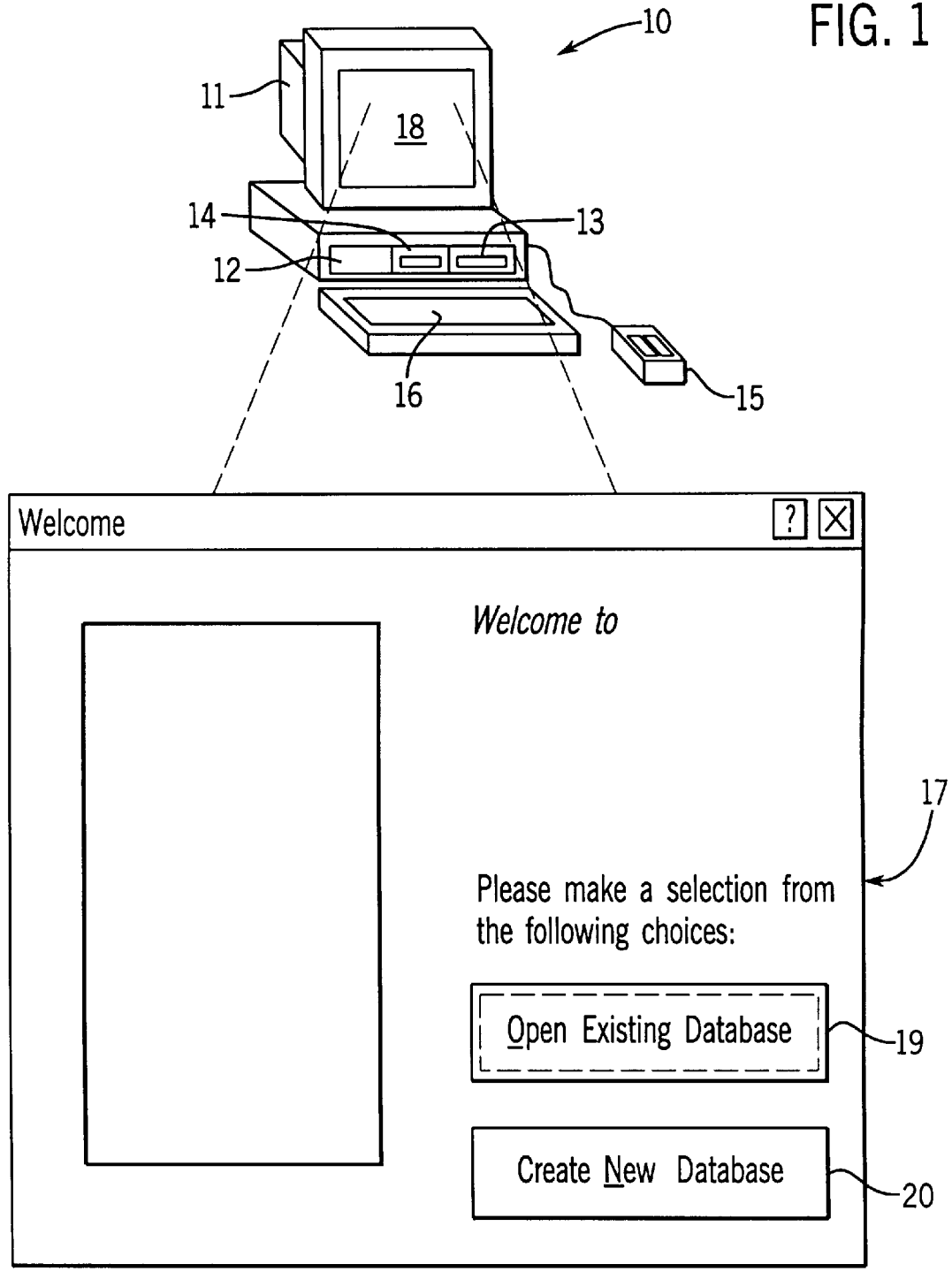
FIG. 1 is a perspective view of a desktop computer with a start-up screen display illustrating the start-up operation of a computer system utilizing the present invention.

Referring to FIG. 1, the method and system of the present invention are embodied in portions of a computer program code which can be installed on conventional and commercially available personal computers. Referring to FIG. 1, typical computer hardware for utilizing the invention includes an IBM-compatible Pentium 100 Mhz computer 10, including 32 Mb of RAM (not shown), an SVGA-compatible color monitor 11 having a screen 18, a 650 Mb or greater capacity hard disk drive 12, a 3.5-inch floppy disk drive 13, a 4x CD-ROM 14, a Microsoft or Microsoft-compatible mouse 15, a suitable keyboard 16, and suitable graphics and network interface cards (not shown). Many other types of hardware configurations known in the art may also be used.

As used herein, the term "user inputs" shall mean input of user commands via mouse, keyboard, or other well known input devices for entering commands.

The computer program is an application program that is loaded into hard disk drive 12 and that runs under the Windows 95 or Windows NT operating system. The personal computer may be a desktop or a laptop computer, or another type of personal computer. The Windows 95 and Windows NT operating systems include capabilities for networking of a plurality of computers running the application program. An advantage of the networked system is that all of the computers may access a common set of data. These systems are just examples and the invention may be carried out with other hardware and operating systems as well.

The program also includes import/export functions for transferring data between patient files and database files which already contain patient (customer) data.

The present invention involves development of an application program using a development system and programming language such as Visual Basic Ver. 5.0 available from Microsoft. Using this development system and associated programming tools, programming code is authored in a high-level programming language, and then compiled into an executable code version for storage on diskettes, CD-ROMs or in computer memories. The program may also be downloaded over the Internet.

The operation of this program and method is shown in a number of screen displays seen in FIGS. 1–14. Various corresponding portions of the program code are executed to display the screen displays in FIGS. 1–14 and to perform the functions described herein. The program is started up by double clicking an icon on the Windows 95 desktop to execute a first portion of program code to display a screen display 17 (FIG. 1) for selecting either an existing database document by selecting button 19 or initiating a new database document by selecting button 20. This application program operates with database-type application documents.

Figure 2:
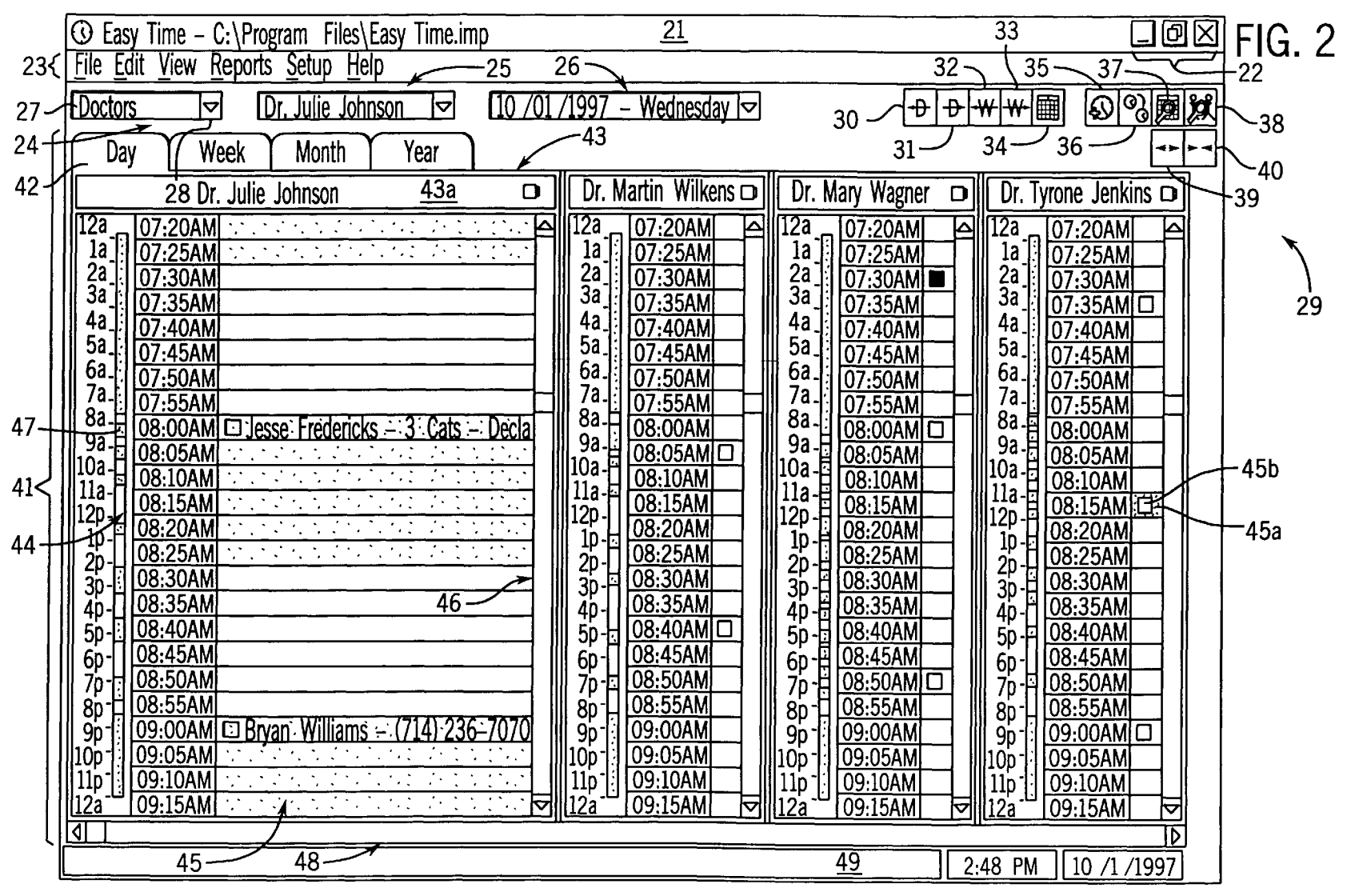

Assuming that an existing database document is available and selected, a second portion of program code is executed to display a screen display 29 of a type illustrated in FIG. 2. The various parts of the screen display will be described with respect to FIG. 2, including portions applicable to subsequent screen displays.

At the top of the screen in the Windows title bar 21, which shows the title of the application program and the open file. Some buttons 22 are located at the upper right hand corner for performing windowing operations, which are not a part of the invention, but are typical for this type of application under this operating system.

Figure 14:
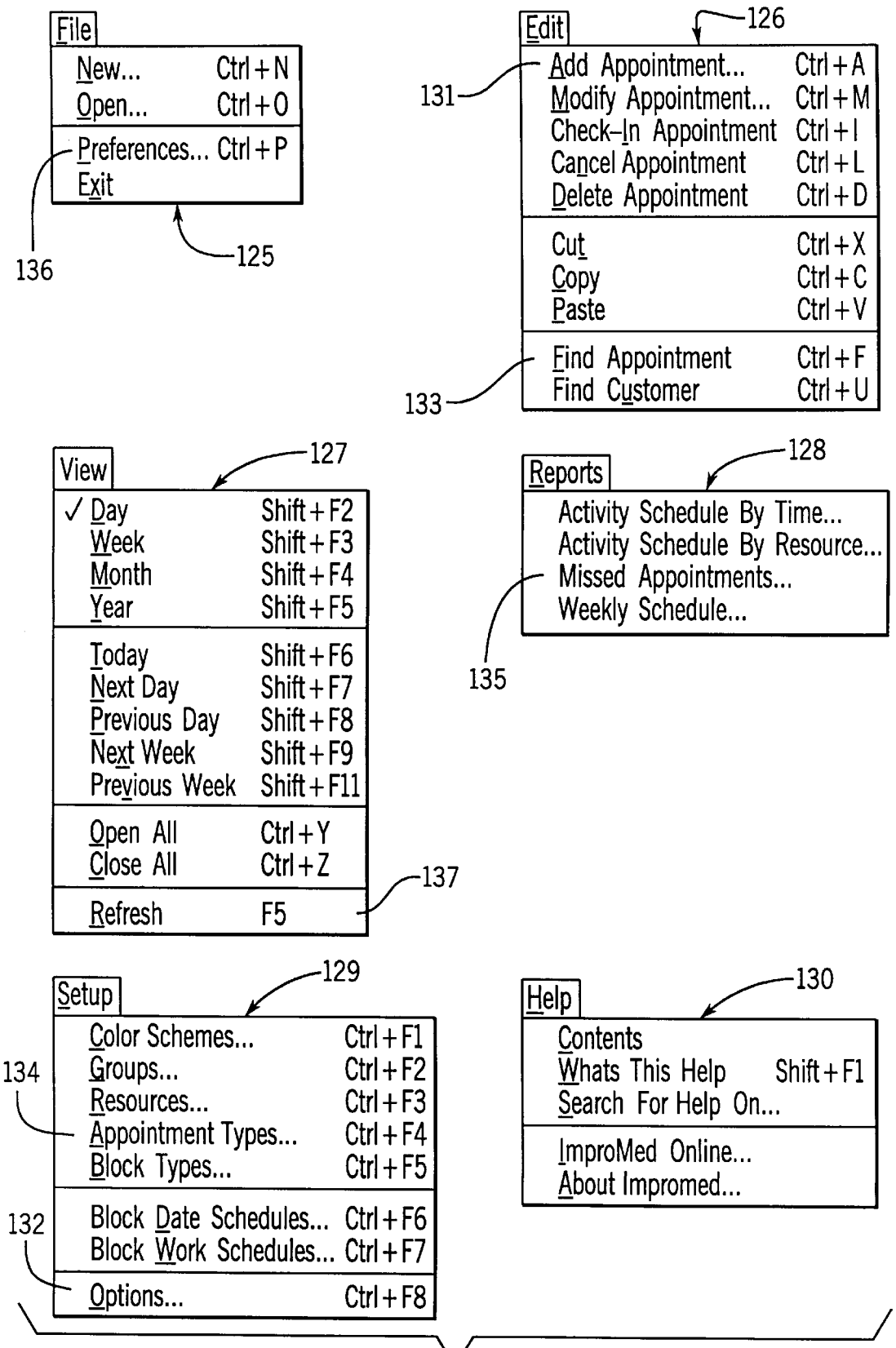
FIG. 14 is an elevational view of a plurality of pull-down menus seen in a menu bar in FIG. 2.

Below the title bar is a menu command bar 23, showing the titles for pull-down menus which contain the mouse-executable commands for the application program. The pull-down menus 125–130 with their command names and key equivalents are illustrated in FIG. 14.

Below the menu command bar are three drop down lists 24, 25, 26, in which the item which is currently selected is shown in a one-line window 27 and a button 28 with an arrow is available for activation to drop down the full list. The three lists are lists for first, groups of persons or resources; second, individual persons or resources within the group; and third, the calendar date. The drop down list for the calendar date 26 further includes drop down lists for month and year, as well as a one-month calendar for selecting days within a month.

"Groups," in this example, include doctors, technicians, groomers, examination rooms and surgery rooms. Resources include individual doctors, individual technicians, the groomers, individual examination rooms and individual surgery rooms.

To the right of the three drop down lists is a tool bar with buttons 30–38 for executing mouse commands, including a "go to previous day" button 30, a "go to next day" button 31, a "go to previous week" button 32, a "go to next day" button 33, a "go to today" button 34, a "new appointment" button 35, an "edit existing appointment" button 36, a "find an existing appointment" button 37 and a "find an existing customer" button 38.

Just below the tool bar are two buttons 39, 40 for expanding and narrowing the width of the individual schedules 43 as described below.

Immediately below the drop-down lists 24, 25, 26 is a multi-tab, multi-dialog panel display 41, including panels for the day of the week, week of the month, month of the year, and the entire year. Other panels may be selected for display by mouse clicking (using the mouse to position the cursor and then operating the left mouse button) on the tabs 42 or selecting commands for week, month and year for the "View" pull-down menu, or by entering their key equivalents from the keyboard.

The panel being displayed in FIG. 2 is for the day of the week, Wednesday, Oct. 1, 1997 (selected in the third drop down list), for a group of doctors (selected in the first drop down list) including Dr. Julie Johnson (selected in the second drop down list). The screen will show schedules 43 for Dr. Johnson, as well as other doctors in the group if space permits. The schedules are shown in FIG. 2 in their unexpanded form, except for Dr. Johnson's schedule.

Each schedule 43 includes a title bar 43a with it being understood that the shape would not have to be rectangular, but could take other forms, and that pictures or icons could be used to identify schedules as well as names.

Each schedule 43 also includes a vertical bar graph 44, sometimes referred to a thermometer graph, with indicia of time along one side. To the right is an appointment file 45 with rows or boxes corresponding to time slots for entry of appointment data opposite a clock time. A vertical scroll bar 46 is provided for scrolling up and down the daily schedule. Once appointments have been entered, a color bar 47 extending for the duration of the appointment appears in the vertical graph. Rows in the appointment file 45 which represent time occupied by a long appointment are color-coded or shaded to signify unavailability. These background colors are defined using the "resource" command under the "Setup" menu 129. Although the colors in the color coding for the vertical bar graph 44 are optional with the user, in this example the following color code is used:

Black—time blocked out (not available)
Background Color—time available for scheduling
Yellow—new appointment, not checked in as yet
Green—checked in for appointment
Red—canceled appointment The advantage of the vertical bar graphs 44 for multiple schedules 43 appearing on the screen at once, is that a quick comparison can be made to see if a common time is available for more than one professional or resource, such as a doctor, and either an examination room or a surgery room.

In addition to the color coding for the status of appointments, a two-color scheme can be used for each resource in which the appointment row 45a in the daily schedule is generally one color, but in which each appointment also includes a check box 45b with the color for the status of the appointment, which also appears in the thermometer bar.

Immediately below the schedules is a horizontal scroll bar 48, which allows scrolling across all schedules in a group, even if the schedules are on a page that is wider than the display area on the screen of the monitor on which they are being displayed. Thus, the user can scroll to schedules which are initially "off the screen" and out of sight. Below the horizontal scroll bar 48 is an application status bar 49, which is part of the application program and which shows the current time and date at the right hand corner. Below this status bar, the operating system status bar may also be seen, although not shown in FIG. 2.

Still referring to FIG. 2, the operator can make an appointment in the "day view" of the schedules by clicking in the status bar opposite the time for starting the appointment. The schedule of the selected resource (Dr. Julie Johnson) will expand in width to show the appointment rows. As a result of the expansion of one schedule, a lesser number of schedules 43 may be visible in the display area. The selected appointment row will be surrounded by a border (not shown) showing that can be typed into. As an alternative, the cursor can be positioned over the appropriate appointment row, and with a right hand button mouse click, cause a pop-up menu with commands for entering the appointment data.

Figure 3:
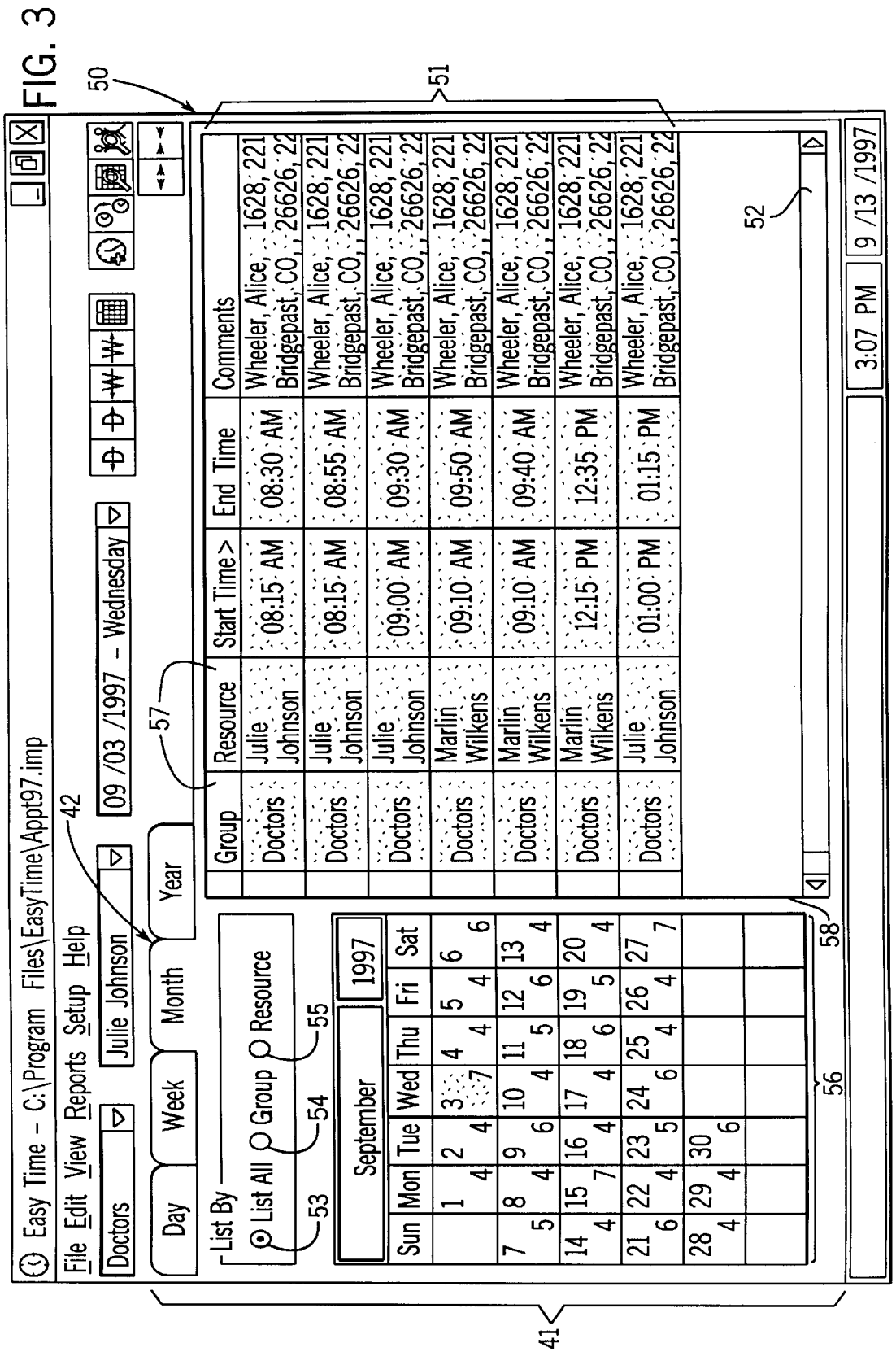
FIG. 3 is an elevational view of a "month view" screen display for the application program running on the computer of FIG. 1.

Referring to FIG. 3, by clicking on the month tab 42 of the multi-tab display 41, another portion of program code is executed to display the panel 50 for a "month view". This panel 50 includes a "list by" dialog section with three radio buttons 53, 54, 55 for listing appointments by "list all," "group" and "resource". Using the "list all" command, all appointments for the month can be displayed in a database file 51 of appointments organized by individual fields, such as group, resource, start time, end time and comments. A horizontal scroll bar 52 is provided beneath the display area in which comments may extend further than the area available for display on the screen 18 (FIG. 1).

The operator of the computer can then further select appointments for a group or resource for the month using the "list by" buttons 53, 54, 55 (FIG. 3). Below the radio buttons is a monthly calendar 56 showing calendar dates and a corresponding number of appointments for each date. The selection of the date acts as a constraint or limit on the appointments which are shown in the display area 58 to the right.

When viewing the appointment schedule in the "month" view, as seen in FIG. 4, the operator can effect changes to the appointment schedule in one of three ways. First, the fields 57, such as group, resource and start time in the appointment list can be sorted by ascending or descending order. Mouse clicking on the title of the field such as "start time" changes the sort order to the opposite order. An arrow showing the sort order is displayed next to the title of each column (field) that is sorted. Second, the mouse can be used to drag the bottom horizontal separator line 59 of a row down to make a row larger for holding more information. Third, a right hand mouse button can be clicked to display a pop-up menu 60 with commands for editing an appointment.

Figure 5:
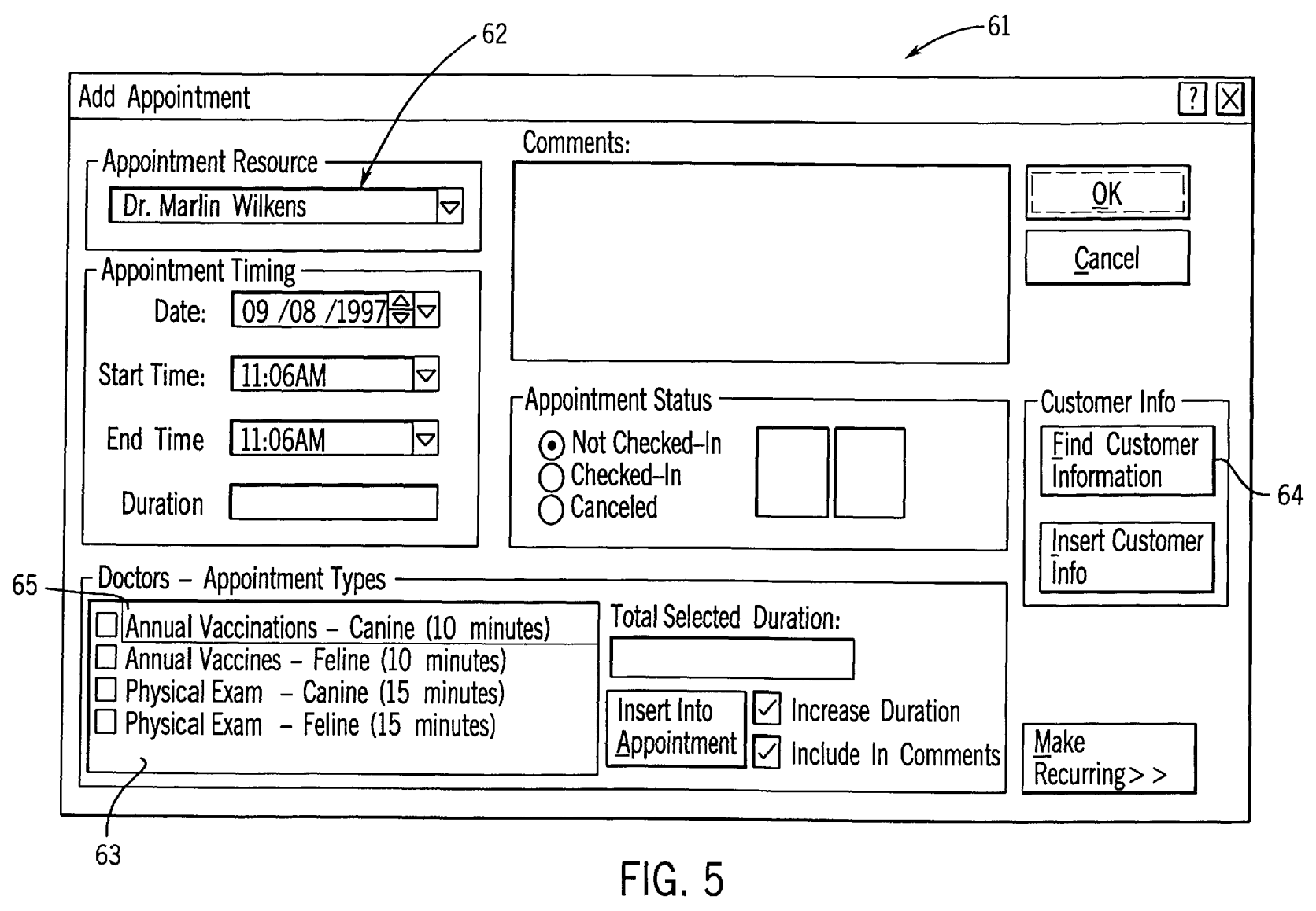

If an "Add Appointment" command 131 in the "Edit" pull-down menu 126 (FIG. 14) is executed, a screen display 61 as seen in FIG. 5 is displayed. This dialog combination box allows selection of the individual resource from a drop-down list 62, selection of a type of appointment 65 from an appointment type list 63 and selection of a patient when a find customer information button 64 at the right is selected. The appointment type 65 lists the duration of the appointment. The scheduler sets the start and end times based on the start time desired by the client (customer) and the standard duration specified in the appointment type 65.

When the find customer information command button 64 is executed by mouse or keyboard, a search dialog box is displayed to search for the patient record. In the veterinary example, there may be multiple animal patients listed under one client or owner. When a patient name is selected from a list found from the search dialog box, a patient list window 70 is displayed as seen in FIG. 6.

In FIG. 6, at the top of the patient list window 70 is a color-code box 71 for showing the overall status of this client, which is a logical result of considering all of the statuses of the individual patients, and signalling if any one requires attention. The program will automatically sort this list by status with the most serious status at the top. Below the client name and overall status is a list of the individual patients 72 with their corresponding color-coded status. The color code in this example is as follows:

Red=Schedule appointment ASAP
Yellow=Alert, information will soon expire
White=Information is up to date Below patient status are the statuses 74 of ordinary treatments 73, such as vaccinations, which are scheduled on a regular basis. Icons 74 are provided for the status of individual treatments 73 and overall health status as follows. The traffic signal icons include a stop sign 75 meaning that information has expired and an appointment should be scheduled as soon as possible, a caution sign (not shown) meaning that information will expire soon and that more appointments can be scheduled now, and a green light sign 77 meaning that information is up to date and that no further appointments are necessary. The "question mark" icon 76 means that necessary information has not been entered in the computer system and further data must be entered before any determination can be made. A "red cross" icon 78 means that the patient has a medical condition that warrants special consideration.

The application program allows the operator to set certain parameters or load certain information which can then be used over and over again in scheduling appointments. For example, the "Setup" menu 129 (FIG. 14) includes an "Option" command 132. When executed by the mouse or equivalent key strokes, this command will cause display of an "Options" window 80 (FIG. 7) and a multi-tab set of dialog panels 81 with tabs 82 for general, password, status colors, customers, and group/resource sorting.

Figure 7:
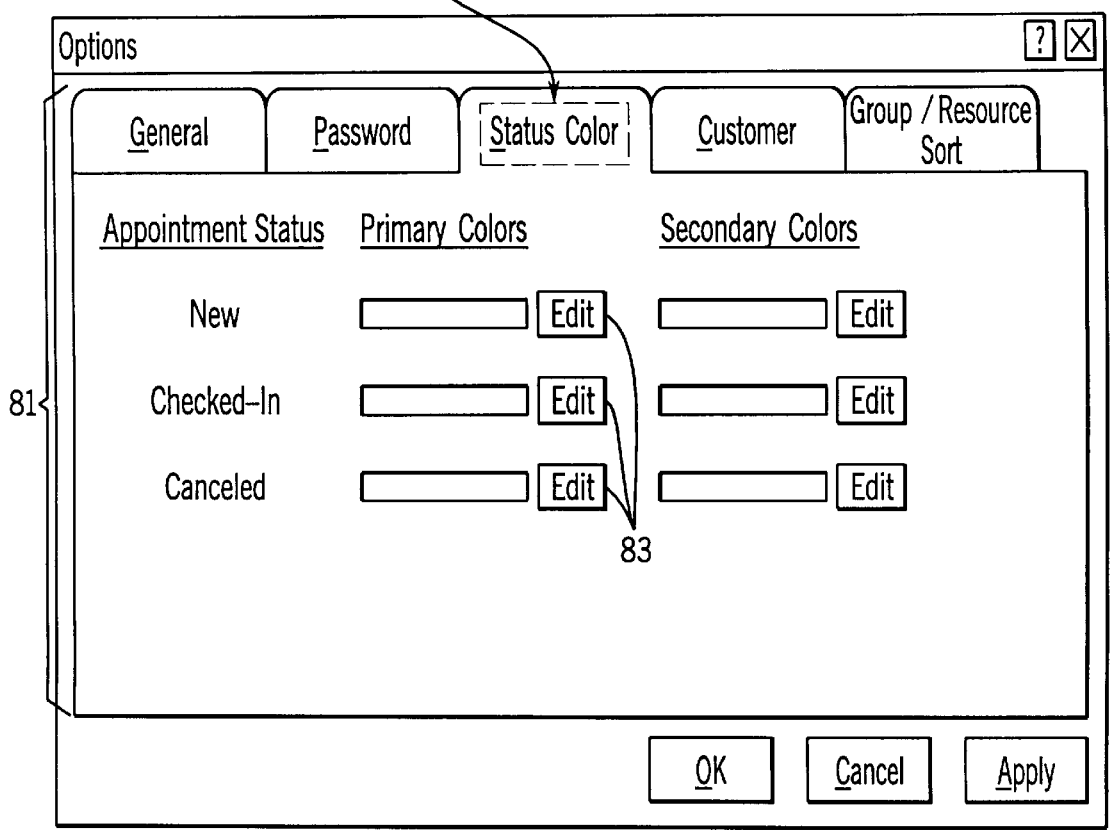
FIG. 7 is an elevational view of a "Status Color" panel of an "Options" multi-panel dialog box for the application program running on the computer of FIG. 1.

Referring to FIG. 7, when the "Status Color" tab 82 is selected, another portion of program code is executed to display a panel 81 for setting the appointment status colors for new, checked-in and canceled appointments, using edit buttons 83 to cause display of a color window (not shown) with a palette of colors displayed in a matrix for selection of an individual color by mouse clicks or keystrokes. The status color of each appointment will appear in the thermometer bar graph 44 of each schedule (FIG. 2). The color also appears in a small check box (not shown in FIG. 2) in the entry in the appointment row 45a. In FIG. 2, the operator can click on the first color showing a "not checked-in" appointment to jump to the first such appointment. The "canceled" status and the "not checked in" status allows the operator or office manager to summarize results at the end of the day.

Figure 8:
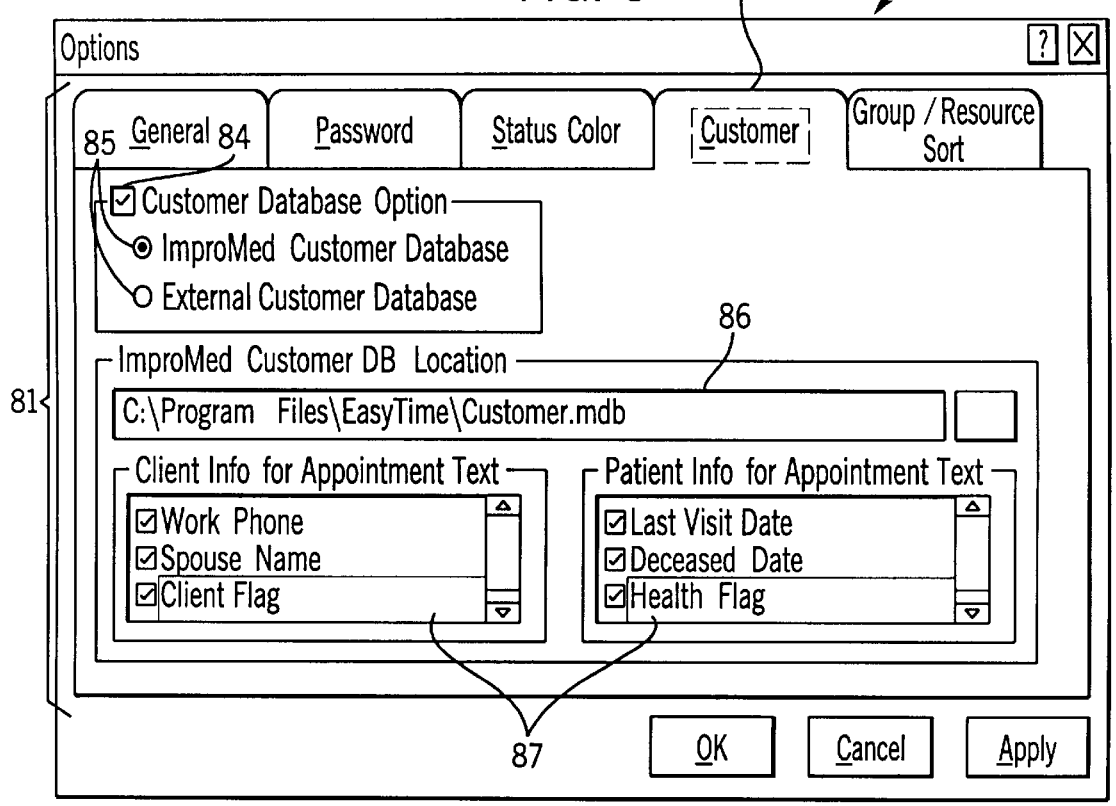
FIG. 8 is an elevational view of "Customer" panel of an "Options" multi-panel dialog box for the application program running on the computer of FIG. 1.

Referring next to FIG. 8, when the "Customer" tab 82 is selected, another portion of program code is executed to display a dialog panel that includes a check box 84, radio buttons 85, a file locator window 86 and lists 87 for selecting fields of data from an external database file to be imported as a database file for the appointment scheduling application. Alternatively, a file of patients and appointments can be developed completely within the scheduling program, however, most offices will have a pre-existing file of patient data.

Figure 9:
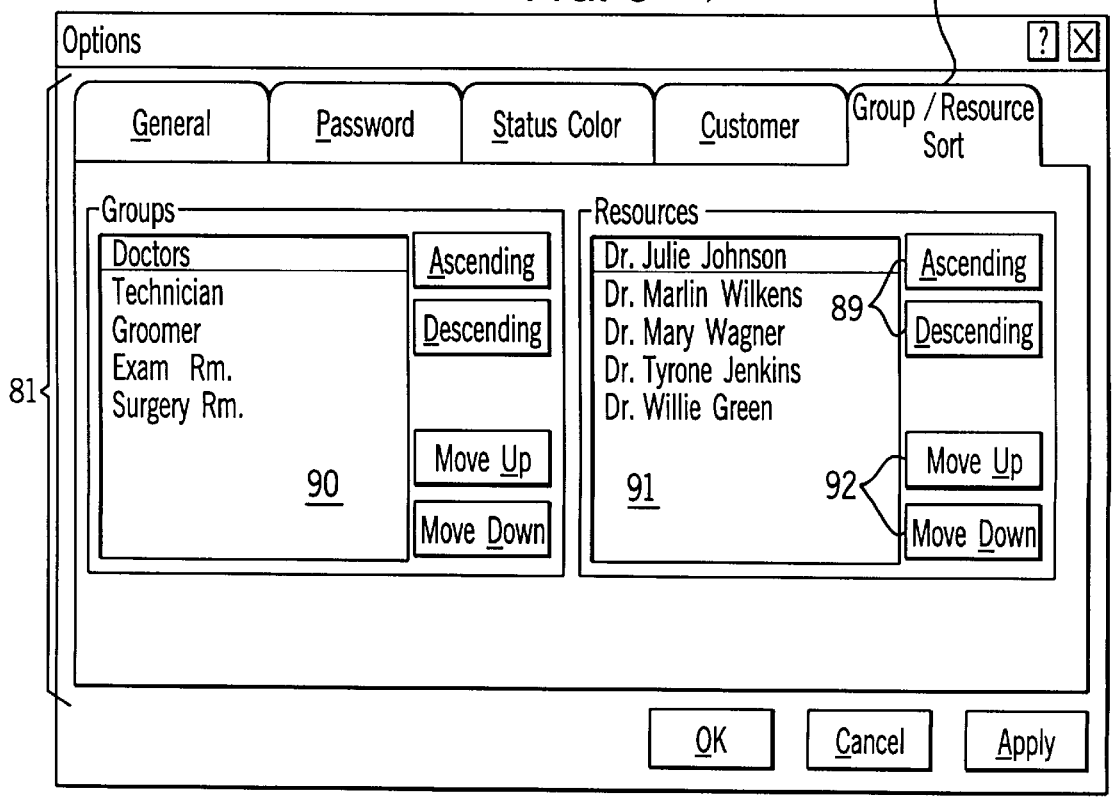
FIG. 9 is an elevational view of a "Group/Resource Sort" panel of an "Options" multi-panel dialog box for the application program running on the computer of FIG. 1.

Referring to FIG. 9, when the "Group/Resource Sort" tab 82 is selected, another portion of program code is executed to display a dialog panel with lists 90, 91 of groups and resources which can be sorted by ascending or descending order using button 89. The dialog panel 81 also allows the changing of the order of appearance of the groups and resources in the menu lists 90 by moving a group or resource up or down the list in the dialog box using the command buttons 92. Groups or resources are added through the "Group" and "Resource" commands in the "Setup" menu 129. The group and resource organization allows sorting in the monthly schedule (FIGS. 3, 4) by group and resource which is very advantageous in scheduling new appointments among many other previous appointments, as well as coordinating resources.

The above-mentioned operations were carried out under the "Options" command 132 in the "Setup" menu 129 (FIG. 14). Another advantageous command is the "Appointment Types" command 134. When this command is selected and executed, another portion of program code is executed to display a dialog box 95 (FIG. 10), including a window 96 for entry of appointment types such as vaccination, surgeries and examinations. Windows 97, 100 and data boxes 98, 99 are provided for entering appointment descriptions, duration in hours and minutes and an assigned group for conducting the appointment. These appointments can be set up by one specialist, and then used by other office personnel over and over again simply by selecting the appointment type from a list. In making the appointment (FIG. 5), the appointment maker sets the start time, selects the appointment type, and then enters an end time based on the preset appointment duration. This appointment will then be displayed in an individual schedule 43 of the type seen in FIG. 2, with the duration and the color for that type of appointment represented on the thermometer type bar graph 44.

Referring to FIG. 11, a "Find Appointment" command 133 is executed in the "Edit" menu 126 (FIG. 14) to execute another portion of program code to display a dialog box 101 for searching for appointments. This box includes an entry window 102 for entering a search string, a window 103 for entering a selected group, a window 104 for entering a selected resource, data boxes 105, 106 for entering a date range, data boxes 107, 108 for entering a time range, status boxes 109 for searching for all appointments 110 of a certain appointment status. The appointments 110 located in a search are displayed in a display area 111 at the bottom of the screen, and a pop-up menu 112 can be displayed with a right button mouse click on the appointment to be modified.

Figure 12:
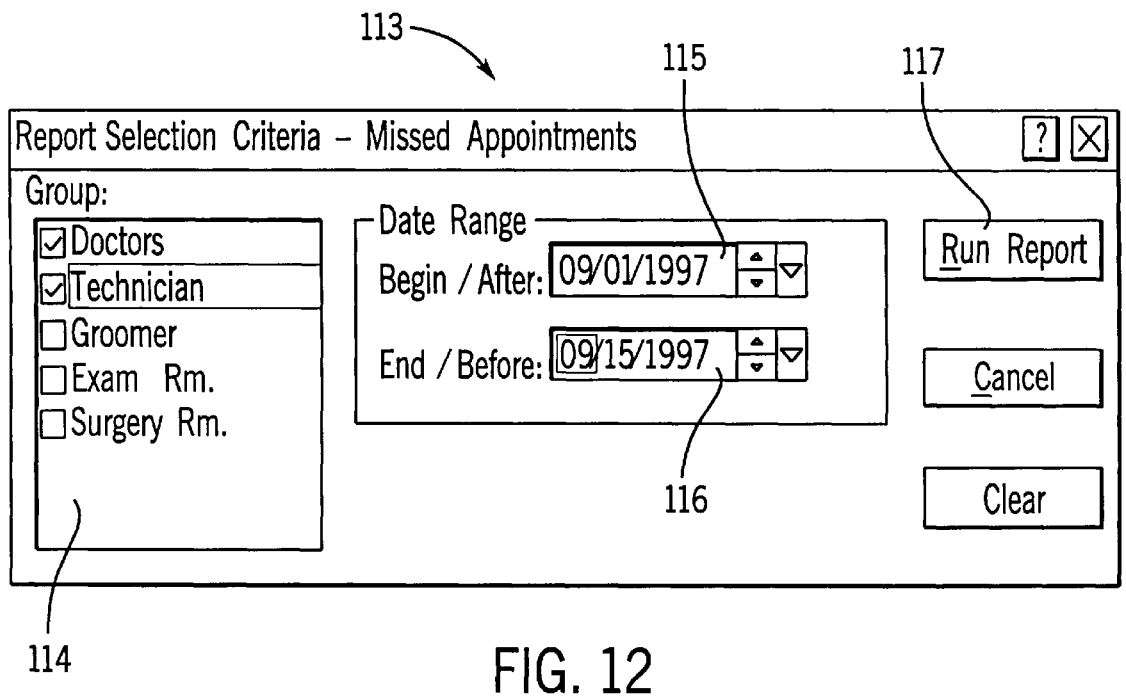
FIG. 12 is an elevational view of a "Missed Appointments" dialog box for the application program running on the computer of FIG. 1.

Referring to FIG. 12, under the "Reports" menu 128 (FIG. 14), a "Missed Appointments" command 135 can be selected and executed to display a dialog box 113 for selecting the group in window 114 and date range in data boxes 115, 116 for generating a list of all missed appointments within these parameters. The report is sent to a printer to be printed and saved in a report file with the "Run Report" command button 117.

Figure 13:
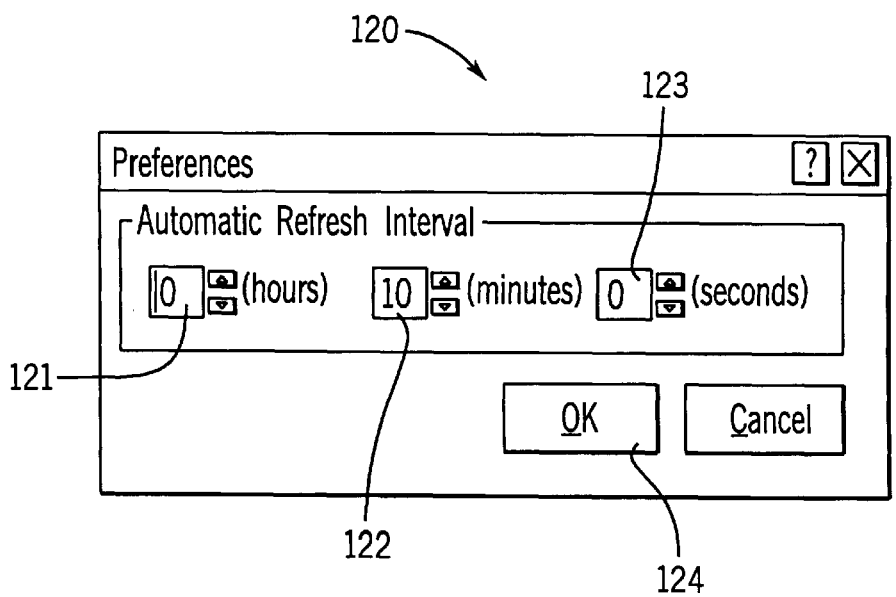
FIG. 13 is an elevational view of a "Preferences" dialog box for the application program running on the computer of FIG. 1.

Referring to FIG. 13, the schedules are refreshed on the screen from data that is input on the computer running the program or a computer connected by networking to the computer displaying the schedules. The refresh rate of the daily schedules can be controlled by executing the "Preferences" command 136 under the "File" menu 125 (FIG. 14) and displaying the dialog box 120 seen in FIG. 10 and then entering number for the refresh rate in hours (if that long), minutes and seconds in boxes 121, 122 and 123 and executing the "OK" button 124. The schedules can also be refreshed instantaneously by operating the F5 command key on the keyboard to execute the refresh command 137.

This has been a detailed description of various examples of how the invention can be carried out. Those of ordinary skill in the art will recognize that the various details may be modified in arriving at other detailed embodiments, in that these embodiments will come within the scope of the invention.

For example, while the invention has been described in relation to a veterinary practice, other embodiments include other types of medical practices, as well as other types of businesses, such as auto repair or beauty salons. In this respect, the term patient or client should be understood to be the equivalent of customer in these other businesses. Similarly, the term "health" as used encompasses conditions beyond medical health for these other types of businesses.

Keeping in mind these equivalents of the embodiments covered by the invention described in detail herein, the following claims are made.

We claim:

1. A method of operating a computer, wherein in response to a first user input, said method comprises displaying a screen display having i) a plurality of appointment schedules side-by-side for a corresponding group of persons or resources, each appointment schedule including separately from others of the plurality of appointment schedules a) a title bar identifying the person or resource, b) a vertical time graph extending over at least one day with colored vertical bars of variable length corresponding in color and length to corresponding types and lengths of appointments, respectively, and c) a plurality of appointment rows corresponding to time slots available for appointments during said day.

2. The method of claim 1, in which the plurality of schedules extend horizontally across a page for a distance that is wider than a display area on the computer screen; and
further comprising displaying at least one horizontal scroll bar for the plurality of appointment schedules to allow scrolling across a width of the page of appointment schedule, wherein said page is wider than the display area on the computer screen.

3. The method of claim 1, further comprising, in response to further user inputs, storing appointment information specifying a procedure including the name of the procedure, the standard time duration and a group to which the procedure pertains; and
in scheduling individual appointments, in response to further user inputs, displaying said appointment information in a list applicable to the group for selection along with the previously stored standard time duration.

4. The method of claim 1, further comprising, in response to further user inputs, displaying a patient dialog box including identification of a plurality of patients, and a color designating overall status of the patients.

5. The method of claim 1, further comprising, in response to further user inputs, displaying a patient dialog box including a health warning icon for any health warning conditions and a plurality of status icons representing status of certain medical conditions associated with an individual patient.

6. The method of claim 1, further comprising, in response to further user inputs executing a "find appointments" command, displaying a "find appointments" dialog box for receiving data defining a specific resource, a date range, a time range and an appointment status to define the scope of the retrieval of appointments in the database file for display.

7. The method of claim 1, further comprising, in response to further user inputs for executing a "missed appointments" command, displaying a dialog box for receiving data defining a specific group and a date range to limit the appointments listed in a missed appointments report.

8. The method of claim 1, further comprising, in response to user inputs for executing an "options" command, displaying a dialog box for receiving data defining criteria for importing patient data from a patient database file.

9. The method of claim 1, further comprising, in response to user inputs for executing a "preferences" command, displaying a dialog box with boxes for receiving data defining a rate at which new data input into the computer system is used to update the appointments file.

10. The method of claim 1, wherein each of the plurality of schedules can be expanded or narrowed in width to control how much of the appointment rows are displayed for a respective individual schedule.

11. A method of operating a computer, comprising:
response to user inputs, associating individual persons or resources with corresponding groups, for sorting and arrangement of schedules or appointments related to said persons or resources; and
further comprising in response to further user inputs, displaying a "month view" screen display including a monthly calendar showing the number of appointments for each day, a file of appointments organized in columns by group and resource, and radio buttons responsive to user inputs for displaying an appointment list for listing all appointments for the month or for listing appointments by at least one of: by day, by group and by resource.

12. The method of claim 11, further comprising, in response to further user inputs, changing at least one of i) an order of listing the groups in a list and ii) an order of listing of the resources in a list for resources.

13. The method of claim 11, further comprising, in response to further user inputs, sorting the file of appointments by field in ascending or descending order.

14. The method of claim 11, further comprising, in response to at least one user input when the appointment file is displayed, displaying a pop-up menu of commands for modifying appointments in the appointment list.

15. A computer program stored in a storage medium for causing a computer to operate according to portions of program code stored in the storage medium, the stored computer program comprising:
a first portion of program code stored in the storage medium for displaying a screen display having a plurality of appointment schedules side-by-side for a corresponding group of persons or resources, each appointment schedule including separately from others of the plurality of appointment schedules i) a title bar identifying the person or resource, ii) a vertical time graph extending over at least one work day with colored vertical bars of variable length corresponding in color and length to corresponding types and lengths of appointments, respectively, and iii) a plurality of appointment rows corresponding to time slots available for appointments during said work day.

16. The stored program of claim 15, wherein said plurality of schedules extend horizontally across a page for a distance that is wider than a width of a corresponding display area on the computer screen; and
further comprising a second portion of program code stored in the storage medium for displaying at least one horizontal scroll bar for the group of appointment schedules to allow scrolling across a width of the page of appointment schedules, wherein said page is wider than the width of the corresponding display area on the computer screen.

17. The stored computer program of claim 15, further comprising a second portion of program code responsive to user inputs to store appointment information specifying a procedure including the name of the procedure, a standard time duration and a group to which the procedure pertains; and
further comprising a fifth portion of program code for scheduling individual appointments in which appointments are displayed in a list applicable to the group for selection along with the previously stored standard time duration.

18. The stored computer program of claim 15, further comprising a second portion of code program responsive to user inputs to display a patient dialog box including identification of one or more patients, and a color designating overall status of the one or more patients.

19. The stored computer program of claim 15, wherein a second portion of program code is responsive to user inputs to display the patient dialog box including a health warning icon for any health warning conditions and a plurality of status icons representing status of certain medical conditions associated with an individual patient.

20. The stored computer program of claim 15, further comprising a second portion of program code responsive to user inputs for executing a "find appointments" command to display a find appointments dialog box for receiving data defining a specific resource, a date range, a time range and an appointment status to define the scope of the search for appointments in the database file for display.

21. The stored computer program of claim 15, further comprising a second portion of program code responsive to user inputs for executing a "missed appointments" command to display a dialog box for receiving data defining a specific group and a date range to limit the appointments assembled in a missed appointments report.

22. The stored computer program of claim 15, further comprising a second portion of program code responsive to user inputs for executing a "options" command to display a dialog box for receiving data defining criteria for importing patient data from a patient database file.

23. The stored computer program of claim 15, further comprising a second portion of program code responsive to user inputs for executing a "preferences" command to display a dialog box for receiving data defining a rate at which new data input into the computer system is used to update the appointments file.

24. The stored computer program of claim 15, further comprising a second portion of program code stored in the storage medium for responding to a user input to expand or narrow how much of the appointment rows are displayed for a respective individual schedule.

25. A stored computer program stored in a storage medium for causing a computer to operate according to portions of program code stored in the storage medium, the stored computer program comprising:

a first portion of program code stored in the operational medium and responsive to user inputs to associate individual persons or resources with corresponding groups, for sorting and arrangement of schedules or appointments related to said persons or resources; and further comprising a second portion of program code responsive to user inputs to display a "month view" screen display including a monthly calendar showing the number of appointments for each day, a file of appointments organized in columns by field, and radio buttons responsive to user inputs for displaying an appointment list for listing all appointments for the month or for listing appointments by day, by group or by resource.

26. The stored computer program of claim 25, wherein the first portion of program code is responsive to further user inputs to change an order of listing the groups in a list and to change the order of listing of the resources in a list.

27. The stored computer program of claim 25, wherein said second portion of program code is responsive to user inputs to sort the file of appointments by field in ascending or descending order.

28. The stored computer program of claim 25, wherein said second portion of program code is responsive to user inputs to display a pop-up menu for modifying appointments in the appointment list.

* * * * *